United States Patent [19]

Rockett et al.

[11] 3,959,212

[45] May 25, 1976

[54] RADIO-OPAQUE DENTAL RESTORATIVE MATERIAL

[75] Inventors: Thomas J. Rockett, East Greenwich, R.I.; John J. O'Connell, Tustin, Calif.

[73] Assignee: American Hospital Supply Corporation, Evanston, Ill.

[22] Filed: June 3, 1974

[21] Appl. No.: 475,607

[52] U.S. Cl................................ 260/42.53; 32/15; 106/35; 106/306
[51] Int. Cl.².......................................... A61K 5/06
[58] Field of Search............ 32/15; 106/35, 52, 306; 423/331; 260/42.53

[56] References Cited
UNITED STATES PATENTS

| | | | |
|---|---|---|---|
| 3,539,526 | 11/1970 | Bowen | 260/42.53 |
| 3,540,126 | 11/1970 | Chang et al. | 32/15 |
| 3,715,331 | 2/1973 | Molnar | 32/15 X |
| 3,801,344 | 4/1974 | Dietz | 32/15 X |
| 3,826,778 | 7/1974 | Dietz | 32/15 X |
| 3,827,901 | 8/1974 | Griffin et al. | 106/306 |

*Primary Examiner*—Donald E. Czaja
*Assistant Examiner*—S. M. Person
*Attorney, Agent, or Firm*—Dawson, Tilton, Fallon & Lungmus

[57] ABSTRACT

A radio-opaque composite material for use as a dental restorative which consists essentially of a conventional polymerizable resin binder and catalysts in admixture with a finely-divided inorganic filler capable of being coupled to the binder. The filler comprises a crystalline silicate containing barium in the crystalline composition. Calcium barium silicate in crystalline form is set forth in disclosing the best known mode for practicing the invention.

5 Claims, 1 Drawing Figure

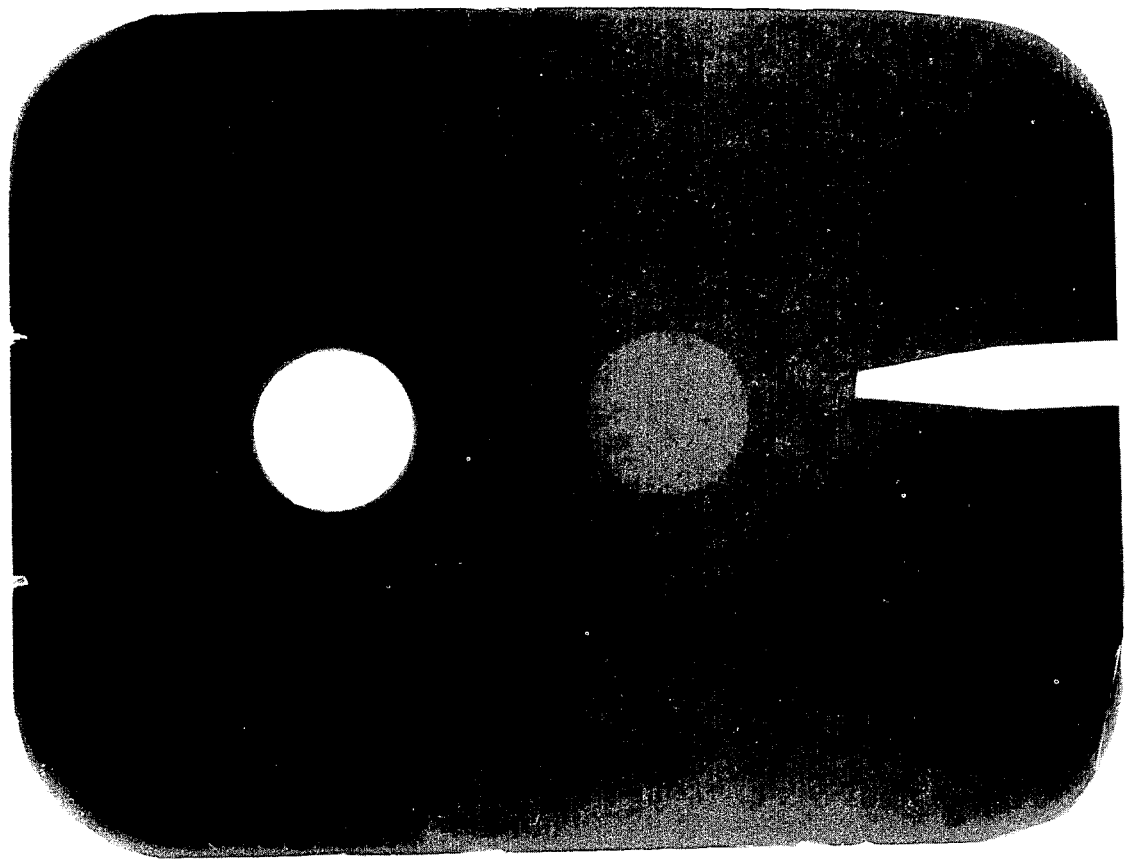
IMPROVED DENTAL COMPOSITE     PRIOR ART COMPOSITE     METAL INSTRUMENT TIP
FIG. I

RADIO-OPAQUE DENTAL RESTORATIVE MATERIAL

BACKGROUND

Ceramic reinforced polymer matrix composites have become well known in recent years and are now generally regarded as being superior to the silicate cements and direct filling resins which were previously used as dental restorative materials. Such composites normally consist of a methacrylate-based system in which a silica glass filler is covalently bonded to a resin matrix, or to a coupling agent which is covalently bonded to both. The finely-divided filler material reinforces the resin matrix and, when used to the 80 percent level, greatly reduces polymerization shrinkage and thermal expansion in comparison with the previously-used direct filling resins. In terms of stability, insolubility, strength, and general performance, the ceramic reinforced polymer matrix composites have overcome many of the objections raised in connection with earlier dental restorative materials.

The aesthetic superiority of modern dental composites is accompanied by at least one disadvantage, however. Not only are such dental restorations difficult or impossible to distinguish from natural tooth surfaces by normal visual inspection, they are also hard to distinguish by x-ray analysis. Ideally, a superior dental restoration should be indistinguishable from the natural tooth under ordinary light but should stand out clearly in an x-ray photograph so that a dentist can easily distinguish the limits of the restoration in searching out any carious dentin that may underlie the filling.

Efforts to provide radio-opaque dental composites have met with only very limited success. Glass fillers formulated to contain enough barium to achieve appreciable radio-opacity are otherwise unsatisfactory because of the solubility of the glass at high concentrations of barium. Since the solubility decreases at lower concentrations, it has been found possible to prepare barium-containing glasses in which no appreciable leaching of the barium will occur; however, in such a case the barium concentration is so low that radio-opacity is virtually lacking (see photograph).

The solubility of barium-containing glass fillers has led some workers to incorporate barium carbonate in the filler composition. While barium carbonate has the advantage of being relatively insoluble, it has the offsetting disadvantages of being relatively soft and, in general, of weakening the composite. In its carbonate form, the barium does not become part of the reinforcing filler but simply serves as a radio-opaque additive. If the barium carbonate is included in sufficient amounts to produce satisfactory radio-opacity, then an unacceptable weakening of the composite may result, whereas if the amount is kept low enough to maintain the strength and durability of the product, radio-opacity is marginal.

SUMMARY

An important object of the present invention lies in providing a composite material for producing radio-opaque dental restorations without the shortcomings and disadvantages previously described. More specifically, it is an object to provide a barium-containing composite which is distinctly radio-opaque without having the attending disadvantages of high solubility and weakness which would be encountered if existing commercial formulations were altered to achieve a similar level of radio-opacity.

The direct filling composite material of the present invention differs from conventional composites by reason of the filler composition which essentially includes a finely-divided crystalline silicate containing barium in the filler's crystalline composition. Specifically, the filler contains, or may consist entirely of, calcium barium silicate in crystalline form. If less radio-opacity is desired, the filler composition may also include a selected amount of calcium silicate (wollastonite) in intimate relationship therewith. The inclusion of wollastonite has the further advantage of insulating or protecting the calcium barium silicate from exposure to water, thereby even further lowering the already low solubility of the barium in the crystalline matrix.

Other objects and advantages will become apparent as the specification proceeds.

ILLUSTRATION

FIG. 1 is a reproduction of an x-ray photograph of two circular chips and the tip of a metal dental instrument. One of the chips is composed of a conventional and commercially-available dental composite material in which the filler includes a barium-containing glass; the other chip is composed of the dental restorative material of the present invention. The tip of the dental instrument is included only for purposes of comparison.

DESCRIPTION

A direct filling dental composite prepared in accordance with this invention comprises a finely-divided inorganic filler, a polymerizable binder, and a catalyst system for polyermizing that binder. Both the binder and the catalyst system may be entirely conventional. Additionally, a suitable silane coupling agent may be used to achieve covalent coupling between the binder resin and filler material. Since information concerning the formulation and preparation of such resin binders, coupling agents, and catalyst systems are well known in the art, they will be only briefly described herein.

A typical formulation for the resin binder would consist of a crosslinking dimethacrylate monomer (such as the monomeric reaction product of 4,4'-isopropylidenediphenol and glycidyl methacrylate commonly called BIS-GMA), along with a comonomer for reducing the viscosity of the liquid phase (such as methylmethacrylate or ethyleneglycol dimethacrylate). For the catalyst, a co-catalyst system, such as an organic peroxide used in conjunction with an aromatic tertiary amine, has been found particularly effective although a single catalyst system might conceivably be used. In a co-catalyst system, the amine is commonly referred to as an accelerator but, since such accelerator functions generally as a co-catalyst, both terms are believed appropriate herein. A typical co-catalyst system might consist of benzoyl peroxide as one component and N,N'-dimethyl-3,5-dimethyl aniline as the other. A silane coupling agent, such as trialkoxysilane containing an organic function, may be used to promote adhesion between the binder and filler material in a manner as fully disclosed in the prior art although it is to be understood that the use of a silane coupling agent may not be necessary or even desirable in all cases and that techniques are available, or may become available, for the direct bonding of the filler to the polymeric matrix.

Other illustrations of binder and catalyst systems suitable for use in practicing the present invention are set forth in detail in the prior art, particular reference being made to U.S. Pat. Nos. 3,066,112, 3,539,533, 3,539,526, and 3,740,850.

As already mentioned, the composite of this invention is characterized by the fact that the finely-divided solid inorganic filler material is a crystalline (not amorphous) silicate which contains barium as part of its crystalline structure. A particularly effective filler material has been found to be crystalline calcium barium silicate of the formula $Ca_2Ba(SiO_3)_3$, such material being particularly effective because of its low solubility in water (when incorporated into a composite system the solubility of the composite is less than 0.8 percent after 72 hours in boiling water), its substantially white appearance, and its capability of being covalently coupled to the binder with the use of a conventional silane coupling agent. However, it is believed that other crystalline barium-containing silicates might be used such as, for example, a ternary silicate such as celsian $BaAl_2Si_2O_8$, or a quaternary crystalline silicate such as $BaMgCa_2Si_2O_8$.

The filler for the dental composite may consist entirely of the crystalline barium silicate material, or may be composed of a two phase combination of that silicate with another silicate compatible therewith such as, for example, calcium silicate (wollastonite). A particularly effective form of wollastonite, and its method of preparation, are disclosed in co-pending co-owned application Ser. No. 416,808, filed Nov. 19, 1973. As disclosed in that application, wollastonite in its natural form (Form A) will comminute to fibrous crystals which tend to stack upon each other. To overcome such problems, pseudowollastonite (Form B) may be prepared by reacting sodium metasilicate with calcium chloride to produce a precipitate of calcium silicate which can then be fired to produce Form B wollastonite.

While the filler may include wollastonite, the mixture should consist at least predominantly of crystalline barium silicate so that the barium silicate content is at least 15 mole percent and preferably exceeds 20 mole percent. A filler meeting those requirements may be prepared by reacting sodium metasilicate with calcium chloride and barium chloride to cause co-precipitation of calcium silicate and barium silicate. After washing and drying, the precipitate is then fired to a temperature above 1,150° C. and below 1,300° C., a temperature sufficient to sinter the precipitated silicate composition but not to melt it. After heating for a suitable interval, the material is quenched in air or water and is then milled until the particles are of a size no greater than approximately 50 microns, and preferably within the range of 2 to 20 microns. The result is a crystalline filler composition consisting essentially of calcium barium silicate $Ca_2Ba(SiO_3)_3$; whether the filler consists entirely of such material, or consists predominantly of such material with calcium silicate in intimate relation therewith, depends on the proportions of the original reactants.

A second method may also be used to prepare the desired calcium barium silicate. That method involves three steps: First, the calcium silicate is prepared by reacting sodium silicate and calcium chloride to form a precipitate which is then fired at a temperature between 1,150° C. and 1,300° C. for approximately 30 minutes to produce wollastonite; second, pure barium silicate is prepared by reacting barium hydroxide with a 30 percent colloidal silica solution to form a precipitate which is fired at about 1,400° C. for 20 minutes; third, the barium silicate and calcium silicate (wollastonite) as so prepared are mixed in a 2-to-1 mold ratio, heated at about 1,350° C. for approximately 20 minutes, then slowly cooled to about 1,310° C. over a 2 hour period, and then cooled slowly to about 1,200° C. After maintaining the material at approximately 1,200° C. for about one half hour, the melt is quenched in water. The resulting material is then milled until the particles are of a size no greater than about 50 microns, and preferably within the range of about 2 to 20 microns. X-ray defraction analysis of such material shows it to be very low in unreacted barium silicate and to have relatively low water solubility characteristics.

The final direct filling composite material is prepared by mixing the finely-divided filler with the components of the resin and catalyst systems described above, preferably after treating the filler with a suitable silane coupling agent in the manner well known in the prior art. It is to be noted that such a filler material has a relatively high refractive index (approximately 1.64), substantially higher than the refractive index of the polymeric resin binder (about 1.52 to 1.58). the mismatch in the refractive indices results in a restoration which is relatively opaque but such opacity has been found aesthetically desirable for many purposes. It is to be noted, however, that where a greater degree of surface translucence is desired, the composite of the present invention may be used as part of a double-layered system of the type described in co-owned co-pending application Ser. No. 416,807, filed Nov. 19, 1973. In such a system, the radio-opaque filler would be used only in preparing a composite which forms a sub-layer at the site of restoration. Before the resin of that sub-layer has fully cured, a surface layer composed of the same resin and catalysts but a different inorganic filler, such as a conventional silica glass filler, would be applied to the site over the sub-layer. The result would be a two-layered restoration having a common resin phase.

Other aspects and advantages of the invention will be apparent from the following illustrative examples:

EXAMPLE 1

A radio-opaque filler for use in preparing a dental composite embodying the invention may be prepared by dissolving 212 grams of sodium metasilicate in 2,500 milliliters of distilled water. A second solution is prepared by dissolving 76.6 grams of $CaCl_2$ and 76 grams of $BaCl_2$ $2H_2O$ in 750 milliliters of distilled water. The two solutions are then mixed to form a coprecipitation of calcium silicate and barium silicate in a ratio of approximately 2 to 1. After evaporating to dryness and heating at 600° C. for one hour, the material is washed to remove sodium chloride from the precipitate. The precipitate is then dried in an oven at 110° C. for approximately 5 hours. Thereafter, the dried precipitate is heat treated at a temperature between 1,150° C. and 1,300° C. for approximately 1 hour. After the heat treatment, the material is quenched in water and cooled to room temperature. The crystalline calcium barium silicate (which may have some calcium silicate associated with it) is then ball milled until an average particle size of less than 50 microns is obtained.

The solubility in water of the filler material when incorporated into a composite system is approximately 0.8 percent over a period of 72 hours in boiling water.

EXAMPLE 2

A dental composite using the filler of Example 1 was prepared using a resin binder made by mixing 1.5 grams Permasorb MA, 70.0 grams BIS-GMA, 15.0 grams trimethylolpropane-trimethacrylate, 15.0 grams ethylene glycol dimethyacrylate, and 0.05 grams 2,5-di-t-butyl-p-cresol (BHT). The ingredients of the binder were gently heated and mixed until a homogeneous mixture was formed. Equal amounts of the resin binder were then mixed with correspondingly equal amounts of the filler (treated with a conventional silane coupling agent) to produce a two component system, to one of which was then added a catalyst, and to the other of which was added an accelerator, as follows.

Part A of the two component system was prepared by first mixing 1.8 grams benzoyl peroxide (catalyst paste) and 45.0 grams of the base resin and, after a homogeneous mixture was formed, slowly added with continual mixing 180 grams of the treated filler powder. Mixing was continued until a homogeneous paste was formed.

Part B of the system was prepared by first mixing 0.675 grams m-tolyl diethanolamine and 45 grams of the base resin until a homogeneous mixture was formed, and then slowly adding (with continuous mixing) 180 grams of the treated filler powder. Mixing was continued until a homogeneous paste was formed.

The final step of preparing the composite was undertaken by mixing equal quantities of parts A and B and molding the uncured resin into disc-shaped chips. Curing occurred in approximately 5 minutes.

Composite chips of similar size were molded using a commercial barium-containing composite marketed under the designation "Smile" by Sybron Corporation of Rochester, New York. FIG. 1 is an enlarged photographic print comparing the radio opacity of two chips of the different composites by x-raying such chips on dental film using conventional dental x-ray equipment. The results of such x-ray analysis shows the dental composite of the present invention (left side of x-ray) to have relatively high x-ray opacity in contrast to the chip formed of the conventional barium-containing composite (center). The tip of a metallic dental instrument (right side) is included in the x-ray photograph for purposes of further comparison.

EXAMPLE 3

A composite embodying the invention, containing only trace quantities of free barium silicate and having solubility of less than 0.5 percent over a period of approximately 72 hours in boiling water, and also having a relatively high level of radio opacity, may be prepared by the following steps:

Preparation of $CaSiO_3$

1. Dissolve 2.2 grams of $Na_2SiO_3$ $5H_2O$ in approximately 2,500 ml water.
2. Dissolve 115 grams of $CaCl_2$ in one liter of water.
3. Combine the solutions prepared in steps 1 and 2 while stirring.
4. Filter slurry to remove liquid.
5. Redisperse precipitate in distilled water and filter again.
6. Repeat step 5, 8 or 9 times.
7. Dry precipitate in oven until anhydrous.
8. Fire dried material in oven at 1,300° C. for approximately 30 minutes, then quench in water.
9. Grind to a fine particle size (under 50 microns).
10. Store in clean glass container.

Preparation of $BaSiO_3$

1. Dissolve 315.5 grams $Ba(OH)_2$ $8H_2O$ in one liter of water.
2. Mix solution of step 1 with 200.0 ml of Ludox LS (30 percent $SiO_2$).
3. Chill and then decant off liquid.
4. Dry precipitate in oven until anhydrous.
5. Fire at 1,400° C. for approximately 20 minutes and quench in air.
6. Grind to a fine particle size (under 50 microns).

Preparation of $Ca_2Ba(SiO_3)_3$

1. Weigh out 47.5 grams $CaSiO_3$ and 41.3 grams $BaSiO_3$.
2. Mix materials completely and fire at 1,350° C. to form a melt.
3. Cool the melt slowly to 1,310° C. and maintain at that temperature for one to two hours. Thereafter, cool slowly to about 1,200° C. and quench in water.
4. Grind material to a suitable size for processing (under 50 microns).
5. Store in clean glass container.

While in the foregoing we have disclosed an embodiment of the invention in considerable detail for purposes of illustration, it will be understood by those skilled in the art that many of these details may be varied without departing from the spirit and scope of the invention.

We claim:

1. A dental composite consisting essentially of a polymerizable resin binder, a catalyst system for polymerizing said binder, and a finely-divided inorganic filler capable of being coupled to said binder, in which the improvement lies in said filler comprising a crystalline silicate containing barium as part of the crystalline composition thereof and selected from the group consisting of $Ca_2Ba(SiO_3)_3$, $BaAl_2Si_2O_8$, and $BaMgCa_2Si_2O_8$.

2. A dental composite consisting essentially of a polymerizable resin binder, a catalyst system for polymerizing said binder, and a finely-divided inorganic filler capable of being coupled to said binder, in which the improvement lies in said filler comprising a crystalline calcium barium silicate having the formula $Ca_2Ba(SiO_3)_3$.

3. A radio-opaque direct filling dental composite comprising a finely-divided inorganic filler, a polymerizable binder, and catalyst means for polymerizing said binder, wherein the improvement comprises said filler being composed at least predominantly of finely-divided particles of crystalline barium calcium silicate having a barium content of at least 15 mole percent of said filler and having the formula $Ca_2Ba(SiO_3)_3$.

4. The composite of claim 3 in which said finely-divided crystalline silicate particles are of an average size no greater than about 50 microns.

5. The composite of claim 3 wherein said filler has a minor proportion of calcium silicate associated with it.

* * * * *